US00PP12436P2

(12) United States Plant Patent

Amorao et al.

(10) Patent No.: US PP12,436 P2

(45) Date of Patent: Mar. 5, 2002

(54) STRAWBERRY PLANT NAMED 'VENTURA'

(75) Inventors: Amado Q. Amorao, Camarillo; Arnoldo Solis, Jr., Oxnard; Thomas M. Sjulin, Aromas, all of CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/524,580

(22) Filed: Mar. 13, 2000

(51) Int. Cl.[7] ..... A01H 5/00

(52) U.S. Cl. ..... Plt./209

(58) Field of Search ..... Plt./208, 209

(56) References Cited

U.S. PATENT DOCUMENTS

PP6,231 P * 7/1988 Johnson et al. ..... Plt./209

* cited by examiner

*Primary Examiner*—Bruce R. Campell

*Assistant Examiner*—Susan B. McCormick

(74) *Attorney, Agent, or Firm*—Pennie & Edmonds LLP

(57) ABSTRACT

This invention relates to a new and distinct variety of strawberry named 'Ventura'. The variety is similar to the varieties 'E26', 'Montalvo', and 'Baeza'. The variety is distinguished from 'E26', 'Montalvo', and 'Baeza', in particular, by its globose to flat globose habit, medium density, weak to medium vigor, medium leaf glossiness, calyx diameter that is smaller relative to the corolla, semi-erect attitude at first picking, conical to cordate fruit shape, slight differences in shape between the primary and secondary fruit, narrow band without achenes, insertion of the calyx that is in a basin to level, weak to medium adherence of the calyx, and fruit with firm flesh and a small hollow center.

7 Drawing Sheets

1. BACKGROUND OF THE INVENTION

The new variety originated as a result of a controlled cross between the strawberry plants 'Mr. P' (U.S. Plant Pat. No. 5,840) and 'R1' (unpatented Driscoll variety) in an ongoing breeding program, and was discovered as a seedling in a controlled breeding plot at the Driscoll Research Ranch, Ventura County, Calif. in October 1992. The original seedling of the new cultivar was asexually propagated by stolons at the Driscoll Nursery, McArthur, Shasta County, Calif. Propagules were transplanted to a controlled breeding plot in Monterey County, Calif., where it was identified and selected for further evaluation. 'Ventura' was subsequently asexually propagated and underwent further testing at various locations in Ventura County, Calif. for seven years. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Ventura'. The variety is botanically identified as *Fragaria×ananassa*. The new variety is distinguished from other varieties by a number of characteristics as set forth in Tables 1–6.

3. COMPARISON TO SIMILAR VARIETIES

The varieties which we believe to be similar to 'Ventura' from those known to us are 'E26' (unpatented Driscoll variety), 'Montalvo' (U.S. Plant Pat. No. 11,522) and 'Baeza' (U.S. Plant Pat. No. 11,548). There are several characteristics of the new variety that are different from, or not possessed by 'E26', 'Montalvo', and 'Baeza'. The new variety has a globose to flat globose habit, medium density, weak to medium vigor, medium leaf glossiness, a calyx diameter that is smaller relative to the corolla, a semi-erect attitude at first picking, conical to cordate fruit shape, slight differences in shape between the primary and secondary fruit, a narrow band without achenes, insertion of the calyx that is in a basin to level, weak to medium adherence of the calyx, and fruit with firm flesh and a small hollow center.

Plants of 'Mr. P' were more vigorous than those of 'Ventura'. Fruit of 'Mr. P' had poorer shelf-life than those of 'Ventura' by being more orange in color and possessing raised achenes. Plants of R1 were partially everbearing while those of 'Ventura' are everbearing.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
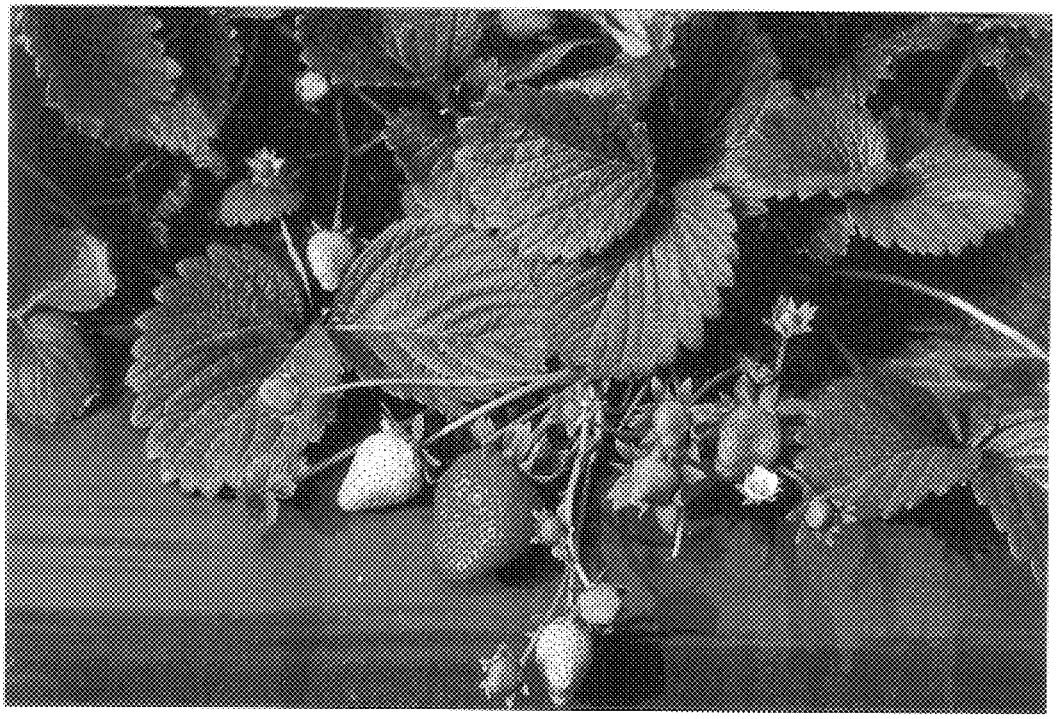
FIG. 1 shows a close-up photo of the whole plant.
Figure 2:
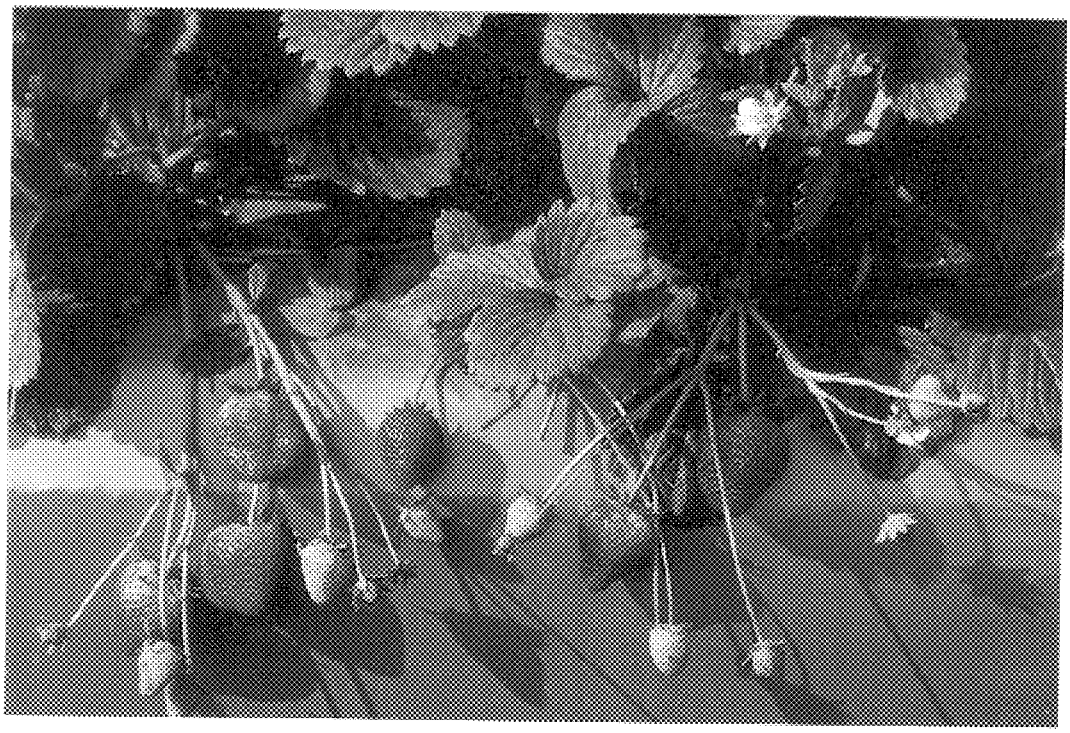
FIG. 2 shows the whole plant.
Figure 3:
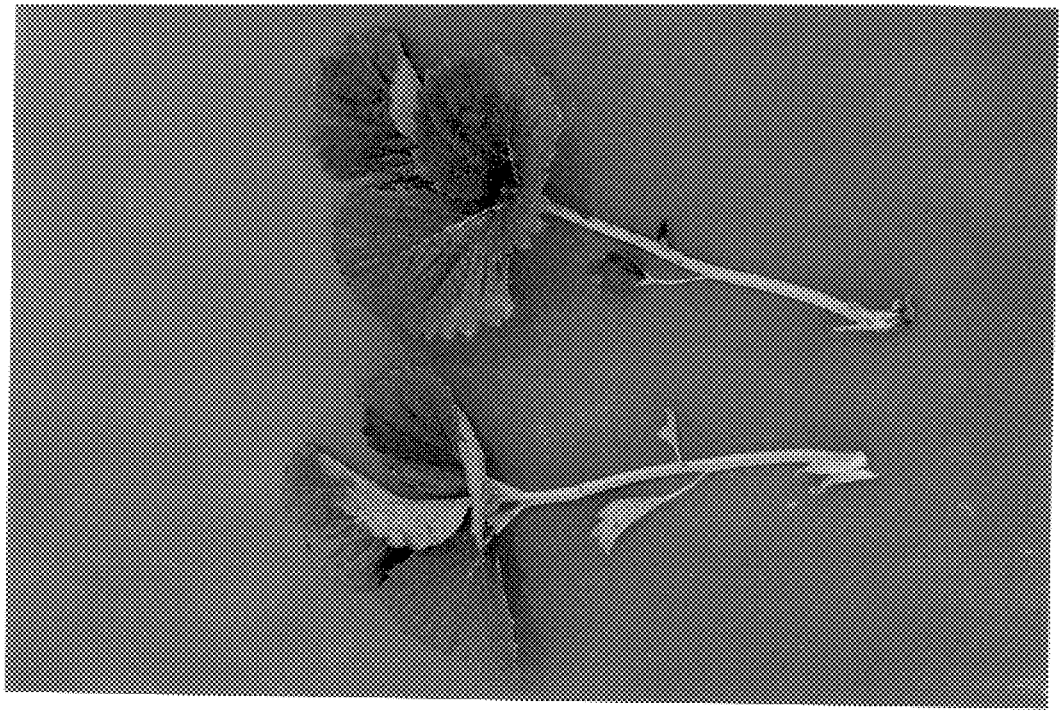
FIG. 3 shows the leaves of the plant.
Figure 4:
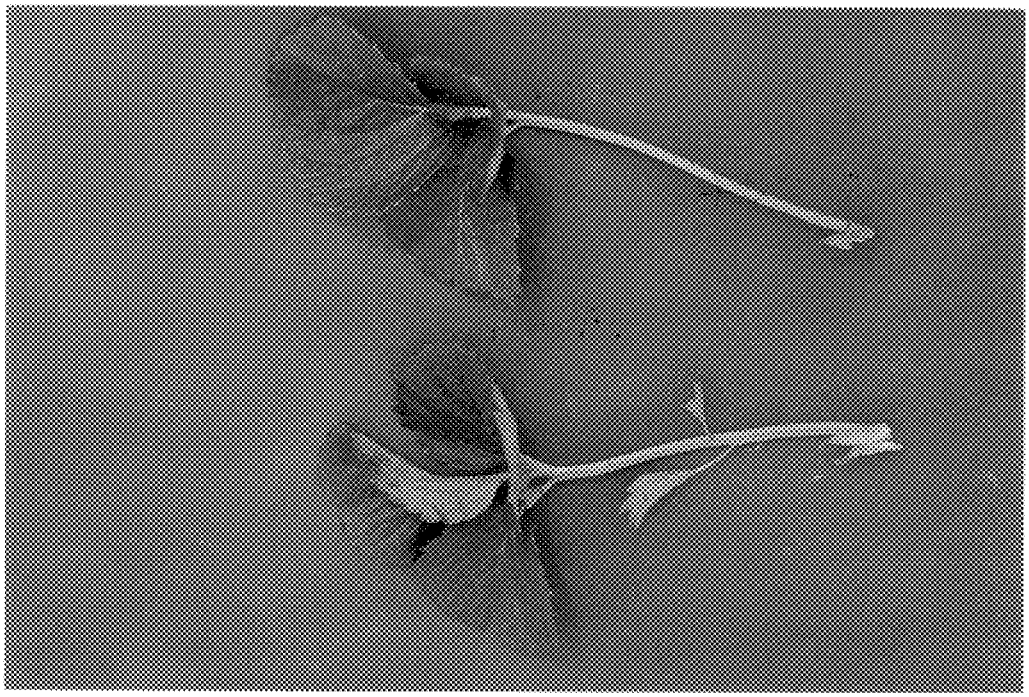
FIG. 4 shows the leaves of the plant.
Figure 5:
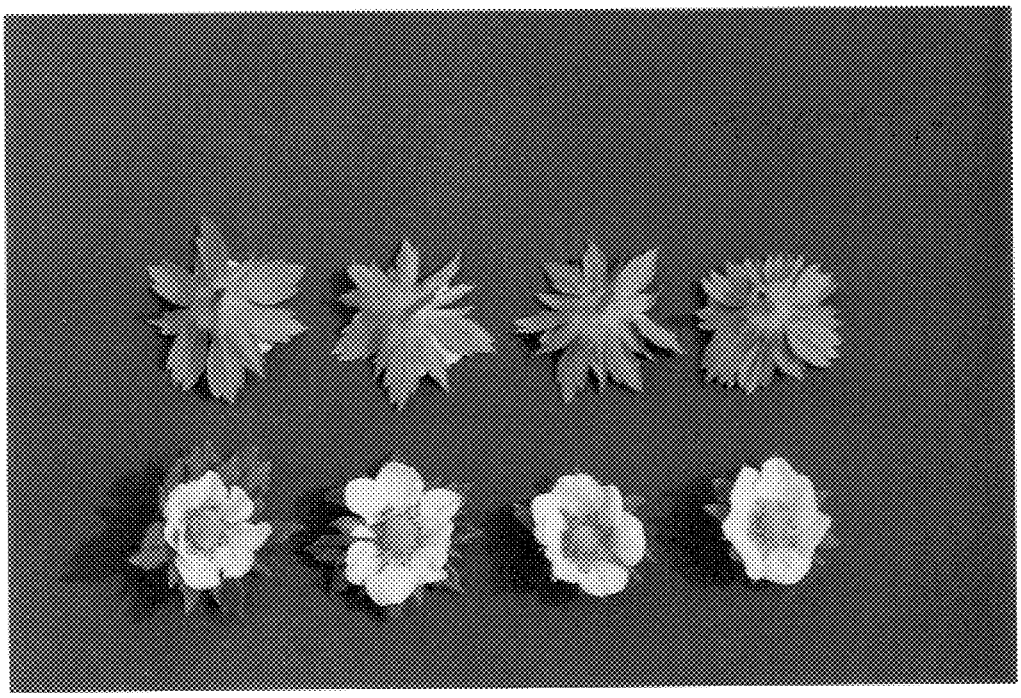
FIG. 5 shows the upper side and under side of the flowers.
Figure 6:
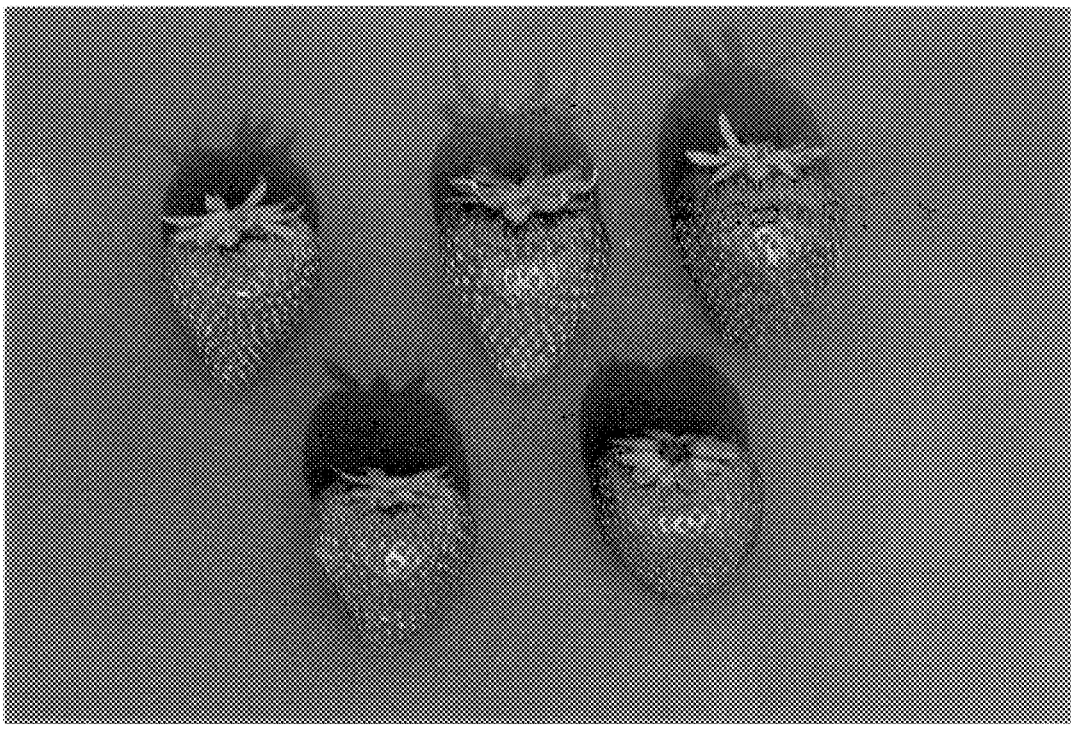
FIG. 6 shows a close-up of the strawberry.
Figure 7:
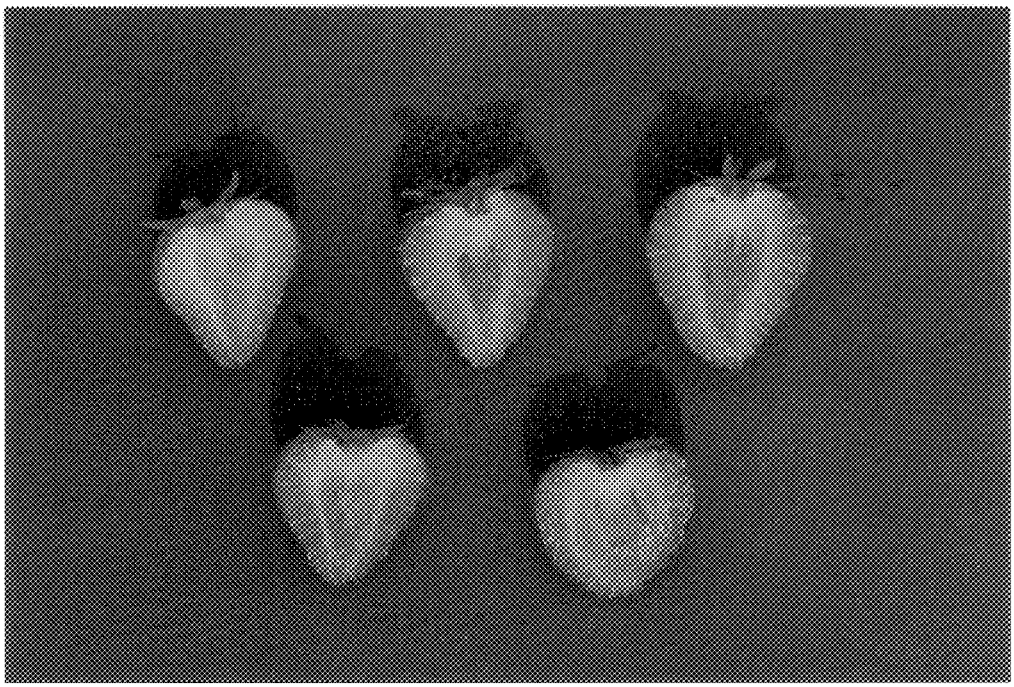
FIG. 7 shows the strawberry in longitudinal cross-section.

The following detailed description of the new variety is based upon observations taken of plants and fruit grown in Ventura County, Calif., U.S.A. Observations of 'Ventura', 'E26', 'Montalvo', and 'Baeza' were taken in side by side comparison in 1999. This description is in accordance with UPOV terminology. Color designations, color descriptions, and other phenotypical descriptions may deviate from the stated values and descriptions depending upon variation in environmental, seasonal, climatic and cultural conditions. Color are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2 and 3. In the tables, the flowers described are secondary flowers except where indicated. The petal color of 'Ventura' is white, 155C in The R.H.S. Colour Chart. The fruit described is the secondary fruit on one year old plants. Fruit and flower measurements are an average of both primary and secondary fruit and flowers.

Table 1 provides information on the plant and fruit characteristics of the new variety 'Ventura' compared with characteristics of 'E26', 'Montalvo', and 'Baeza'. Table 2 provides additional information of the plant and fruit characteristics of the new variety 'Ventura' compared with characteristics of the varieties 'E26', 'Montalvo', and 'Baeza'. Table 3 provides reactions of the new variety to stresses as compared to the varieties 'E26', 'Montalvo', and 'Baeza'. Tables 4 and 5 provide information of the new variety's reaction to pests and diseases, respectively, compared to the varieties 'E26', 'Montalvo', and 'Baeza'. Table 6 provides isozyme characteristics of the new variety as compared to the varieties 'E26', 'Montalvo', and 'Baeza'.

The leaf margin is crenate. Leaf texture is slightly blistered. The shape of the leaf is rounded to broadly ovate. The mid-vein color on the terminal leaflet is yellow green (154C) and the venation pattern is pinate.

The average petiole diameter is 0.37 cm. The average length of the petiole on the terminal leaflet is 1.32 cm.

The petal shape is rounded to broadly ovate. The petal margin is entire. The petal texture is smooth. The shape of the petal apex and base are rounded. The average number of petals per flower is 5.6.

The color of the stipule is yellow-green (145A).

The average sepal length is 1.1 cm. The average sepal width is 0.46 cm. The sepal color is 138A.

The average number of achenes per berry is 286.

TABLE 1

DETAILED COMPARISON OF 'VENTURA', 'E26', 'MONTALVO' AND 'BAEZA'

| | Ventura | E26 | Montalvo | Baeza |
|---|---|---|---|---|
| Plant Characteristics | | | | |
| Height of Plant (cm) | 24.8 | 20.0 | 25.6 | 26.4 |
| Spread of Plant (cm) | 38.9 | 37.5 | 40.4 | 42.6 |
| Number of Crowns | 3.3 | 2.9 | 3.0 | 3.6 |
| Leaf Characteristics | | | | |
| Terminal Leaflet Width (cm) | 8.7 | 8.0 | 9.6 | 9.6 |

TABLE 1-continued

DETAILED COMPARISON OF 'VENTURA', 'E26', 'MONTALVO' AND 'BAEZA'

| | Ventura | E26 | Montalvo | Baeza |
|---|---|---|---|---|
| Terminal Leaflet Length (cm) | 8.3 | 8.0 | 9.5 | 9.5 |
| Terminal Leaflet Length/Width Ratio | 0.96 | 1.00 | 0.98 | 0.99 |
| Number of Teeth/ Terminal Leaflet | 24.6 | 21.2 | 20.6 | 32.2 |
| Color of upper side of leaf | Medium green 137B | Medium green 137A | Light to medium green 147A | Light to medium green 147A |
| Color of under side of leaf | Light green 138B | Light green 138C | Light green 138C | Light green 138B |
| Petiole Lenght (cm) | 17.1 | 14.1 | 15.4 | 16.5 |
| Petiole color | yellow green 145B | yellow green 145A | yellow green 144C | yellow green 144A |
| Bract Frequency | 20% | 40% Typically paired | 20% Typically paired | 70% Typically paired |
| Stipule Length (cm) | 2.9 | 3.1 | 3.5 | 3.6 |
| Stipule Width (cm) | 1.1 | 1.3 | 1.2 | 1.3 |
| Flower Characteristics | | | | |
| Petal Width (cm) | 1.05 | 1.08 | 1.23 | 1.28 |
| Petal Length (cm) | 1.08 | 1.03 | 1.19 | 1.26 |
| Petal Length/Width Ratio | 1.03 | 0.95 | 0.97 | 0.98 |
| Flower Diameter (cm) | 2.76 | 2.70 | 3.08 | 3.15 |
| Calyx Diameter (cm) | 2.49 | 2.63 | 2.82 | 3.00 |
| Fruit Characteristics | | | | |
| Fruit Width (cm) | 3.9 | 3.8 | 4.0 | 3.6 |
| Fruit Length (cm) | 4.0 | 4.0 | 4.6 | 3.9 |
| Fruit Length/Width Ratio | 1.01 | 1.06 | 1.16 | 1.08 |
| Average Berry Size (g) | 26.3 | 23.2 | 27.6 | 21.8 |
| Fruit Skin Color | Red 46A | Orange red 46B | Orange Red 45B | Red 46A |
| Fruit Flesh Color | White & orange red 44A & 155D | White and pale rose 33B & 155D | White and orange red 43A & 155A | White & orange red 42B & 155D |
| Achene Coloration | Yellow to Red 13B to 45B | Yellow to Red 14A to 46A | Yellow to Red 13A to 26A | Yellow to Red 13A to 46A |
| Total Yield (g/plant) | 433 | 503 | 357 | 445 |

TABLE 2

CHARACTERISTICS OF 'VENTURE', 'E26', 'MONTALVO', AND 'BAEZA'

| | Ventura | E26 | Montalvo | Baeza |
|---|---|---|---|---|
| Plant | | | | |
| Habit | globose to flat globose | flat | flat globose | flat globose |
| Density | medium | medium to dense | open to medium | open |
| Vigor | weak to medium | weak | strong | medium |
| Leaf | | | | |
| Shape in cross section | slightly concave | concave to slightly concave | concave | concave |
| Intervenial | strong | strong to | weak to | strong to |

TABLE 2-continued

CHARACTERISTICS OF 'VENTURE', 'E26', 'MONTALVO', AND 'BAEZA'

| | Ventura | E26 | Montalvo | Baeza |
|---|---|---|---|---|
| blistering | | very strong | medium | very strong |
| Glossiness | medium | weak | weak | weak |
| Number of leaflets | 3 only | 3 only | 3 only | 3 only |
| Terminal leaflet margin profile | revolute to flat | revolute to flat | flat | revolute to flat |
| Terminal leaflet shape of base | rounded | rounded | obtuse to rounded | obtuse to rounded |
| Terminal leaflet shape of teeth | obtuse | rounded | rounded | acute to obtuse |
| Stipule pubescence | sparse | sparse | sparse | sparse |
| Petiole pubescence | sparse | sparse | sparse | very sparse to sparse |
| Petiole pose of hairs | outwards | outwards | upwards to outwards | outwards |
| Stolon | | | | |
| Number | few to medium | medium to many | — | — |
| Anthocyanin coloration | medium | medium to strong | — | — |
| Thickness | medium to thick | medium to thick | — | — |
| Pubescence | dense | dense | — | — |
| Inflorescence | | | | |
| Position relative to foliage | level to above | beneath | beneath to level | level to above |
| Diameter of calyx relative to corolla | smaller | same size to larger | smaller to same size | same size to larger |
| Diameter of inner calyx relative to outer | same size | same size | larger | same size |
| Spacing of petals | touching to overlapping | overlapping | overlapping | overlapping |
| Fruiting Truss | | | | |
| Attitude at first picking | semi-erect | prostrate | prostrate | prostrate |
| Length (cm) | 29.8 | 22.1 | 26.4 | 26.9 |
| Fruit | | | | |
| Predominant shape | conical to cordate | conical | conical to almost cylindrical | conical |
| Difference in shapes between primary and secondary fruits | slight | very slight to slight | marked | very slight to slight |
| Band without achenes | narrow | narrow to medium | medium | very narrow to narrow |
| Unevenness of surface | weak to medium | weak | weak to medium on secondary fruit; strong on primary fruit | weak to medium |
| Evenness of color | uneven | slightly uneven | slightly uneven | slightly uneven to even |
| Glossiness | strong | strong | medium to strong | |
| Insertion of achenes | below surface | level with surface | below surface | level to below surface |
| Insertion of calyx | in a basin to level | set above the fruit | set above the fruit | level |
| Pose of the calyx segments | reflexed | reflexed | reflexed | spreading to reflexed |
| Size of calyx in relation to fruit | smaller | smaller | smaller to same size | same size to larger |
| Adherence of calyx | weak to medium | strong | strong | strong |
| Firmness of flesh | firm | soft to medium | medium | medium to firm |
| Evenness of flesh color | slightly uneven | uneven | slightly uneven | uneven |
| Distribution of flesh color | marginal and central | only marginal | marginal and central | marginal and central |
| Hollow center size | small | medium | small to medium | large |
| Sweetness | medium to strong | medium | medium to strong | medium |
| Texture when tasted | fine | medium | fine | medium |
| Acidity | weak to medium | weak to medium | weak to medium | medium |
| Time of Flowering | mid to late August | mid to late August | mid to late August | mid to late August |
| Harvest Interval | Oct. 2–Dec. 18 | Oct. 2–Dec. 18 | Oct. 2–Dec. 18 | Oct. 2–Dec. 18 |
| Type of Bearing | fully everbearing | fully everbearing | fully everbearing | fully everbearing |

5.3 REACTION TO STRESS TABLE 3

TABLE 3

| Reaction to Stress | Ventura | E26 | Montalvo | Baeza |
|---|---|---|---|---|
| high pH | Moderately Resistant | Moderately Resistant | Moderately Resistant | Moderately Resistant |
| high soil salt levels | Moderately Resistant | Moderately Resistant | Moderately Resistant | Moderately Resistant |

5.4 PEST AND DISEASE RESISTANCE AND SUSCEPTIBILITY

TABLE 4

| Reaction to Pests | Venutra | E26 | Montalvo | Baeza |
|---|---|---|---|---|
| *Tetranychus urticae* | moderately susceptible | moderately susceptible | moderately susceptible | moderately susceptible |
| Aphis spp. | susceptible | susceptible | susceptible | susceptible |
| *Lygus hesperus* | susceptible | susceptible | susceptible | susceptible |

TABLE 5

| Reaction to Diseases | Ventura | E26 | Montalvo | Baeza |
|---|---|---|---|---|
| Botrytis fruit rot | moderately susceptible | susceptible | susceptible | susceptible |
| Powdery mildew | highly susceptible | highly susceptible | highly susceptible | highly susceptible |
| Verticillium wilt | susceptible | susceptible | susceptible | susceptible |
| Strawberry Mottle Virus | moderately resistant | moderately resistant | moderately resistant | moderately resistant |
| *Xanthomonas fragariae* | moderately resistant | moderately resistant | moderately resistant | moderately resistant |

5.5 ISOZYME ANALYSIS

In addition to the morphological description above, the new cultivar 'Ventura' has been analyzed to obtain an indication of its genetic makeup to provide further means for identifying the new variety and distinguishing it from some other somewhat similar and/or related strawberry varieties. Specifically, leaf samples of 'Ventura', 'E26', 'Montalvo' and 'Baeza' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme chaaracterization of the three varieties is presented in Table 4, with the letters representing the banding patterns for each enzyme as designated in the above-identified article.

TABLE 6

ISOZYME ANALYSIS FOR 'VENTURA' 'E26', 'MONTALVO', AND 'BAEZA'

| Locus | Ventura | E26 | Montalvo | Baeza |
|---|---|---|---|---|
| PGI | A2 | A2 | A4 | A1 |
| LAP | B3 | B3 | B3 | B3 |
| PGM | C4 | C2 | C4 | C3 |

What is claimed is:

1. A new and distinct variety of strawberry plant, substantially as shown and described.

* * * * *